(12) United States Patent
Kim et al.

(10) Patent No.: US 11,285,000 B2
(45) Date of Patent: Mar. 29, 2022

(54) TOOL FOR TRICUSPID REGURGITATION OPERATION

(71) Applicant: TAU PNU MEDICAL CO., LTD., Yangsan-si (KR)

(72) Inventors: June Hong Kim, Busan (KR); Min Ku Chon, Yangan-si (KR); Jun Oh Kim, Yangan-si (KR)

(*) Notice: Subject to any disclaimer, the term of this patent is extended or adjusted under 35 U.S.C. 154(b) by 102 days.

(21) Appl. No.: 16/528,556

(22) Filed: Jul. 31, 2019

(65) Prior Publication Data

US 2019/0350706 A1 Nov. 21, 2019

Related U.S. Application Data

(63) Continuation of application No. PCT/KR2017/014781, filed on Dec. 15, 2017.

(30) Foreign Application Priority Data

Feb. 1, 2017 (KR) .................. 10-2017-0014420

(51) Int. Cl.
*A61F 2/24* (2006.01)
*A61M 25/01* (2006.01)
(Continued)

(52) U.S. Cl.
CPC .......... *A61F 2/2433* (2013.01); *A61F 2/2466* (2013.01); *A61M 25/01* (2013.01);
(Continued)

(58) Field of Classification Search
CPC .... A61F 2/2433; A61F 2/2466; A61F 2/2442; A61F 2/2445; A61F 2/2451; A61F 2/243;
(Continued)

(56) References Cited

U.S. PATENT DOCUMENTS

2003/0083538 A1* 5/2003 Adams .................. A61F 2/2451
600/16
2003/0233142 A1 12/2003 Morales et al.
(Continued)

FOREIGN PATENT DOCUMENTS

CN 103153230 A 6/2013
JP 2002505140 A 2/2002
(Continued)

OTHER PUBLICATIONS

English machine translation of WO 2015194816; Dec. 2015 (Year: 2015).*

(Continued)

*Primary Examiner* — Wade Miles
*Assistant Examiner* — Mikail A Mannan
(74) *Attorney, Agent, or Firm* — Justin Kim

(57) ABSTRACT

The present invention relates to a device for transcatheter treatment for tricuspid regurgitation. The device for transcatheter treatment for tricuspid regurgitation, according to one preferred embodiment of the present invention, includes: the coronary sinus tube inserted into the coronary sinus; and the tricuspid valve tube traversing the tricuspid valve, wherein the coronary sinus tube and the tricuspid valve tube communicate with each other or are adjacent to each other within a range of predetermined length at an upper side and are separate from each other at a lower side, and a blocking member for blocking a space generated by incomplete closing of the tricuspid valve is provided at a lower part of the tricuspid valve tube or between the coronary sinus tube and the tricuspid valve tube.

27 Claims, 13 Drawing Sheets

(51) Int. Cl.
*A61B 17/34* (2006.01)
*A61B 17/02* (2006.01)
*A61M 25/10* (2013.01)
*A61B 17/00* (2006.01)

(52) U.S. Cl.
CPC ....... *A61B 17/3421* (2013.01); *A61B 17/3468* (2013.01); *A61B 2017/00243* (2013.01); *A61B 2017/0237* (2013.01); *A61F 2/246* (2013.01); *A61F 2/2451* (2013.01); *A61M 25/10* (2013.01)

(58) Field of Classification Search
CPC ...... A61F 2/2427; A61F 2/246; A61F 2/2463; A61F 2/0105; A61F 2/24; A61F 2/011; A61F 2/013; A61B 17/12022; A61B 17/12122; A61B 17/1204; A61M 25/09; A61M 2025/0037
See application file for complete search history.

(56) References Cited

U.S. PATENT DOCUMENTS

| | | | |
|---|---|---|---|
| 2004/0210240 A1 | 10/2004 | Saint | |
| 2008/0195126 A1 | 8/2008 | Solem | |
| 2011/0054597 A1 | 3/2011 | Kim | |
| 2012/0179246 A1* | 7/2012 | Kim | A61F 2/2451 623/2.36 |
| 2013/0211513 A1* | 8/2013 | Rourke | A61F 2/2442 623/2.37 |
| 2013/0325110 A1 | 12/2013 | Khalil et al. | |
| 2015/0100117 A1* | 4/2015 | Bortlein | A61B 17/00234 623/2.11 |
| 2016/0120647 A1* | 5/2016 | Rogers | A61B 17/221 606/139 |
| 2016/0324636 A1* | 11/2016 | Rourke | A61B 17/0401 |

FOREIGN PATENT DOCUMENTS

| | | |
|---|---|---|
| JP | 2002537909 A | 11/2002 |
| KR | 20110023094 | 3/2011 |
| KR | 20110023094 A | 3/2011 |
| KR | 101116867 B1 | 3/2012 |
| KR | 101231140 B1 | 2/2013 |
| KR | 1020130074823 A | 7/2013 |
| KR | 101467373 B1 | 12/2014 |
| KR | 20150144568 A | 12/2015 |
| KR | 1020150144568 A | 12/2015 |
| KR | 1020170044065 A | 4/2017 |
| WO | 0051675 A1 | 9/2000 |
| WO | 2008060553 A1 | 5/2008 |
| WO | 2015194816 A1 | 12/2015 |
| WO | WO 2015194816 * | 12/2015 |

OTHER PUBLICATIONS

International Search Report of PCT/KR2017/014781 dated Mar. 30, 2018.

International Search Report of PCT/KR2015/006040.

* cited by examiner

Note 1 : In the relaxation of the heart
Note 2 : In the contraction of the heart

TOOL FOR TRICUSPID REGURGITATION OPERATION

TECHNICAL FIELD

The present invention relates to a device for transcatheter treatment for tricuspid regurgitation and, more particularly, to a device for transcatheter treatment for tricuspid regurgitation, wherein the device can perform a catheter treatment for tricuspid regurgitation (TR) which is a disease that the tricuspid valve (TV) located between the right atrium and the right ventricle of the heart does not close completely, thereby causing the blood to flow backward in the heart.

BACKGROUND ART

The heart is divided into four chambers: two atria and two ventricles, which are connected to four blood vessels such as the main artery, the main vein, the pulmonary artery and the pulmonary vein, thereby functioning as a passage for blood delivery.

An interventricular septum in the center of the heart separates the heart into two sides: right atrium and right ventricle in one side, and left atrium and left ventricle in the other side. The tricuspid valve is located between the right atrium and the right ventricle, and the mitral valve is located between the left atrium and the left ventricle.

The heart functions as a pump by repeating contraction and relaxation, to allow the blood to flow along the blood vessels. In the systole of the heart, as the blood in the heart flows forwardly to the blood vessels, the blood in the right heart is delivered from the right ventricle to the pulmonary artery and the blood in the left heart is delivered from the left ventricle to the main artery.

However, if a valve between an atrium and a ventricle does not properly operate, the blood of the ventricle flows backward in the systole of the heart, that is, moves toward the atrium. If the tricuspid valve between the right atrium and the right ventricle does not properly operate, the blood of the right ventricle flows backward into the right atrium; this is called "tricuspid regurgitation", and if the mitral valve between the left atrium and the left ventricle does not property operate, the blood of the left ventricle flows backward into the left atrium. This is called "mitral regurgitation".

In tricuspid regurgitation (TR), the blood is not delivered to the pulmonary artery when the heart contracts because the tricuspid valve does not properly operate, thus causing the blood to flow backward into the right ventricle. This is called "tricuspid insufficiency". An outbreak of tricuspid regurgitation is caused since the tricuspid valve does not close completely when it should close because the tricuspid valve between the right atrium and the right ventricle of the heart is stretched or torn, or the chordae tendinae to fix the valve between them is broken.

As typical treatments for the tricuspid regurgitation according to the conventional art, methods of correcting the disease surgically by opening a patient's chest and cutting the heart, that is, an annuloplasty ring method and a DeVega method, have been widely used. However, in these surgical methods, as a surgical treatment highly invasive should be performed, the surgical approach only for the tricuspid valve has not been widely used because the importance of the tricuspid valve is relatively low. That is, when a patient having tricuspid regurgitation underwent a mitral valve surgery or an important heart disease surgery of the coronary arteries, etc., the surgical treatment of the tricuspid regurgitation as described above was done simultaneously.

In this regard, there has been a gradually growing global expectation on research for treatment for tricuspid regurgitation, which is performed using a catheter or a simple device, rather than a surgical method of opening the chest and cutting the heart.

A device for mitral valve cerclage treatment that can be performed with a catheter technique was already proposed by the inventors of the present invention (refer to WO2008/060553 published on May 22, 2008). Also, the inventors of the present invention improved a device for mitral valve cerclage treatment as described above and proposed a device for tricuspid regurgitation surgery (refer to Korean Patent Publication No. 10-2015-0144568), for which a PCT international application was also filed and published in the WIPO gazette (refer to WO2015/194816).

It can be said that the present invention is an improvement in the invention of WO 2015/194816 invented by the inventors of the present invention.

DISCLOSURE

Technical Problem

The present invention has been made to solve the above-mentioned problems of typical tricuspid regurgitation surgery methods according to the conventional art and make improvements to the methods. An object of the present invention is to provide a device for transcatheter treatment for tricuspid regurgitation that can treat the tricuspid regurgitation through a simple catheter technique with minimum invasion and increase an effect of the treatment, thus replacing a surgical method of opening a patient's chest and cutting the patient's heart.

Another object of the present invention is to provide a device for transcatheter treatment for tricuspid regurgitation that can perform the tricuspid regurgitation treatment separately from or together with a mitral regurgitation treatment, which was conceived by improving the device for mitral valve cerclage surgery invented by the inventors of the present invention.

Still another object of the present invention is to provide a device for transcatheter treatment for tricuspid regurgitation, being customized to a patient, in which a size and a position of a blocking member of the device can vary according to the size and the position of the tricuspid valve of each patient.

Yet still another object of the present invention is to provide a device for transcatheter treatment for tricuspid regurgitation, being capable of supporting the tricuspid valve tube stably so as to prevent the tricuspid valve tube from damaging the tricuspid valve.

The present invention is not limited to the objects as described above. Any other objects not mentioned herein could be clearly appreciated by a person having ordinary knowledge in the art to which the present invention pertains, from the description of the invention as described below.

Technical Solution

In order to accomplish the above objects, a device for transcatheter treatment for tricuspid regurgitation according to one exemplary embodiment of the present invention may include the coronary sinus tube inserted into the coronary sinus, and the tricuspid valve tube traversing the tricuspid valve, wherein the coronary sinus tube and the tricuspid valve tube communicate with each other or are adjacent to each other within a range of predetermined length at an upper side and are separate from each other at a lower side, a blocking member for blocking a space generated by incomplete closing of the tricuspid valve is provided at the lower part of the tricuspid valve tube or between the coronary sinus tube and the tricuspid valve tube, and a stopper for preventing an end of the tricuspid valve tube from piercing into an interventricular septum is provided at the lower side of the tricuspid valve tube.

According to another exemplary embodiment of the present invention, a device for transcatheter treatment for tricuspid regurgitation may include the coronary sinus tube inserted into the coronary sinus, the tricuspid valve tube traversing the tricuspid valve, and a sheath tube into which the tricuspid valve tube is inserted in a predetermined region, wherein the sheath tube and the coronary sinus tube are in close contact with each other, and a blocking member for blocking a space (orifice) generated by incomplete closing of the tricuspid valve is provided at the lower part of the tricuspid valve tube or between the coronary sinus tube and the tricuspid valve tube.

According to a still another exemplary embodiment of the present invention, a device for transcatheter treatment for tricuspid regurgitation may include the coronary sinus tube inserted into the coronary sinus, and the tricuspid valve tube traversing the tricuspid valve, wherein the coronary sinus tube and the tricuspid valve tube communicate with each other within a range of predetermined length at an upper side and are separate from each other at a lower side, and a blocking member for blocking a space generated by incomplete closing of the tricuspid valve is provided between the coronary sinus tube and the tricuspid valve tube.

According to a yet still another exemplary embodiment of the present invention, a device for transcatheter treatment for tricuspid regurgitation may include the coronary sinus tube inserted into the coronary sinus, the tricuspid valve tube traversing the tricuspid valve, and a blocking member for blocking a space generated by incomplete closing of the tricuspid valve, the blocking member being provided at a lower part of the tricuspid valve tube or between the coronary sinus tube and the tricuspid valve tube, wherein a position of the blocking member is adjusted by adjusting a position of the tricuspid valve tube, so as to be fitted to the space (orifice) generated by the incomplete closing of the tricuspid valve.

Advantageous Effects

As described above, a device for transcatheter treatment for tricuspid regurgitation according to the present invention is advantageous in enabling simple treatment with minimum invasion, as a catheter treatment technique, enhancing an effect of the treatment and dramatically shortening the patient's recovery period, as compared to the conventional surgery methods of opening a patient's chest and cutting the patient's heart.

Also, as the device according to the present invention can simultaneously perform a function to tighten a mitral annulus, the tricuspid regurgitation treatment can be performed separately from or simultaneously with mitral valve regurgitation treatment. Thus, the present invention is advantageous in being capable of undergoing several treatments satisfactorily with a single device. Further, as a size and a position of a blocking member for blocking a space (orifice) made in the tricuspid valve in the systole of the heart can vary, a doctor may proceed with the treatment according to a size and a position of the space (orifice) caused by incomplete closing of the tricuspid valve which differs from each patient, through an angiography apparatus, providing an advantage in that probability of treatment success can be drastically increased. In addition, as the tricuspid valve can be stably supported, the treatment can be performed without causing any damage by the tricuspid valve tube to the tricuspid valve.

DESCRIPTION OF THE SYMBOLS

Figure 1:
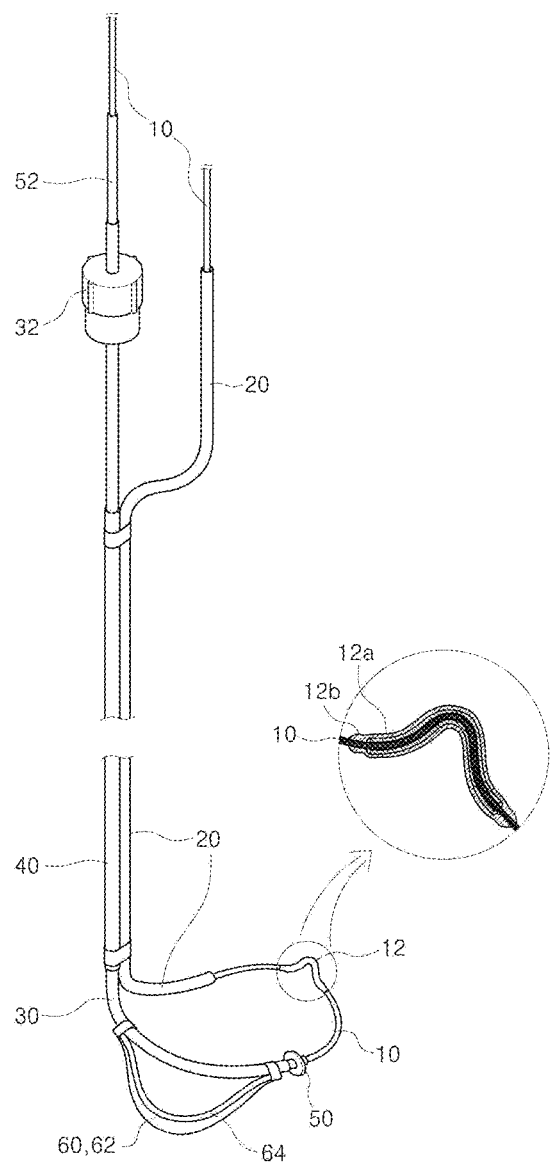
FIG. 1 is a prospective view of a device for transcatheter treatment for tricuspid regurgitation according to one exemplary embodiment of the present invention.

10: Cerclage wire
12: Arch part

12*a*: Arch-shaped protection part
12*b*: Coating part
20: Coronary sinus tube (CS tube)
30: Tricuspid valve tub (TV tube)
32: Holding member
40: Sheath tube
50: Stopper
52: Tube for moving stopper
60: Blocking member
61: Blocking balloon
62: Blocking membrane
64: Support wire
65: Tube for support wire
66: Tube for balloon
67: Balloon control hub

BEST MODE

Advantages and features of the present invention, and methods to achieve them shall be apparent with reference to exemplary embodiments of the present invention hereinafter described in details together with the accompanying drawings. The embodiments of the present invention may be modified in various forms, and the scope of the present invention should not be construed as being limited to the following embodiments. The embodiments of the present invention are just provided for a complete description, thereby fully informing those skilled in the art of the category of the invention. Accordingly, the present invention will be defined on the basis of the category of the claims.

Specific embodiments to realize the present invention will be described in detail with reference to the drawings attached hereto. Without regard to the drawings, the same reference numbers refer to the same elements, and "and/or" covers any and all combinations of the elements mentioned herein, including a combination of respective elements or a combination of one element with two or more elements.

Terms to describe a variety of elements are described, but the elements are not limited to the terms used herein. The elements are merely used to distinguish one element from another. In this regard, a first component described herein may be a second component within the technical concept of the present invention.

The terms used herein are terms used to explain exemplary embodiments of the present invention, rather than to limit the present invention. Also, a singular form may cover a plural form if it is specially mentioned otherwise. Further, "comprises" and/or "comprising" used herein do not exclude existence or addition of one or more other component than the component(s) mentioned.

Without any other definitions, all the terms used herein (including technical terms and scientific terms) may be used to carry the meanings that could be appreciated commonly by those of ordinary knowledge in the art to which the present invention pertains. Also, some terms defined in dictionaries usually used will not be construed ideally or excessively unless they are explicitly particularly defined herein.

Hereinafter, exemplary embodiments of the present invention will be described in details with respect to the accompanying drawings.

FIG. 1 is a prospective view of a device for transcatheter treatment for tricuspid regurgitation according to one exemplary embodiment of the present invention.

Referring to FIG. 1, the device for transcatheter treatment for tricuspid regurgitation of the present invention fundamentally includes a coronary sinus tube 20, a tricuspid valve tube 30, and a blocking member 60. The coronary sinus tube 20 constitutes a portion inserted into the coronary sinus of the heart, the tricuspid valve tube 30 constitutes a portion traversing (intersecting, crossing) the tricuspid valve in and out to reach the interventricular septum. The insides of the coronary sinus tube 20 and the tricuspid valve tube 30 are hollow so as to allow a cerclage wire 10 to be inserted thereinto. The coronary sinus tube 20 and the tricuspid valve tube 30 communicate with each other, or are adjacent to each other within a range of predetermined length at an upper side and are separate from each other at a lower side. The coronary sinus tube 20 and the tricuspid valve tube 30 may be formed of rubber materials, synthetic materials such as soft plastic, etc., or metal materials such as a coil spring, etc. Accordingly, the coronary sinus tube 20 and the tricuspid valve tube 30 are soft and highly ductile, having excellent recovery together with flexibility to allow the coronary sinus tube 20 and the tricuspid valve tube 30 to move according to heart beats. Also, any material having excellent deliverability in cerclage treatment may be used.

The cerclage wire (cerclage suture) 10 is named in a sense that the coronary sinus (CS), the interventricular septum, and the tricuspid valve (TV) are interconnected, like making a loop. As shown in the drawings, the cerclage wire refers to a thread (wire) for connecting the coronary sinus (CS), the interventricular septum, and the tricuspid valve (TV) into one, like making a loop. As materials of the cerclage wire, synthetic materials such as nylon, etc. or metal (stainless steel, metals coated with nylon, etc.) wires may be used. The cerclage wire may be a single wire, or in a form such that a number of thin wires are twisted. The thickness of the cerclage wire may be about 0.5 mm, and the diameter of the tube may be about 2 mm, but they are not necessarily limited thereto.

An arch part 12 is formed on one side of the cerclage wire 10. In most patients (about 80% to 90%), the coronary artery is located beneath the coronary sinus, and the cerclage wire passes through the coronary sinus. In cerclage treatment, if the coronary artery is located beneath the coronary sinus, considerable external pressure is applied by the cerclage wire to the coronary artery. To prevent the external pressure, an arch part 12 is formed thereon. The arch part 12 functions to protect the coronary artery. In the arch part 12 according to the present invention, an arch-shaped protection part 12*a* is inserted into the cerclage wire 10, and an integral arch part whose form is fixed by a coating part 12*b* is used. Polyurethane, polyolefin, silicon, e-polytetrafluoroethylene (e-PTFE), PTFE, etc. for medical purposes are used for the coating part 12*b*.

A blocking member 60 constitutes a portion to block a space (orifice) generated by incomplete closing of the tricuspid valve and is located at a lower part of the tricuspid valve tube, or between the coronary sinus tube and the tricuspid valve tube. Tricuspid regurgitation is a disease that the blood flows backward because the tricuspid valve does not close completely in the systole of the heart. A space (orifice) generated because of incomplete closing of the tricuspid valve in the systole of the heart is blocked by the blocking member 60 of the present invention. As the blocking member 50, a blocking balloon 61 or a blocking membrane 62, etc. may be used. The blocking membrane 62 is shown in FIG. 1. The blocking membrane 62 is made of materials that are suitable for human body and are ductile but not easily torn. Polyurethane, polyolefin, silicon, e-polytetrafluoroethylene (e-PTFE), PTFE, etc. for medical purposes are used for the blocking membrane 62.

In order to hold a shape of the blocking membrane 62, a support wire 62 is provided in the tricuspid valve tube 30. FIG. 1 shows that both ends of the support wire 62 are fixed at the tricuspid valve tube 30, to which is not necessarily limited. It is possible that both ends or one end of the support wire 62 may not be fixed at the tricuspid valve. The support wire 64 may be made of synthetic materials that have a predetermined hardness or metal wires. The thickness thereof may be about 0.5 mm, but not necessarily limited thereto. The support wire may be fixed at the blocking membrane, but the support membrane may be formed doubly, and the support membrane may be configured to insert the support wire thereinto. In this regard, the support wire may also be configured to change a length thereof (refer to the description associated with FIGS. 5 and 6).

A stopper 50 is formed at a lower side of the tricuspid valve tube 30 in order to prevent an end of the tricuspid valve tube 30 from piercing into the interventricular septum. The stopper 50 may be fixed at an end of the tricuspid valve tube 30. However, preferably the stopper 50 may be formed on a lower end of a tube 52 for moving the stopper, and the tube 52 for moving the stopper is structured to be inserted into the tricuspid valve tube 30, as shown in the drawings. In this structure, the stopper moves along the cerclage wire according to movement of the tube for moving the stopper. As this movement causes the tricuspid valve tube to be kept afloat rather than to be in close contact with the periphery of the tricuspid valve, it is possible to prevent damage by the tricuspid valve tube to the tricuspid valve. This configuration will be described in detail referring to FIG. 3.

A sheath tube 40 constitutes a portion into which the upper side of the tricuspid valve tube 30 is inserted. A holding member 32 is held at an upper end of the tricuspid valve tube 30. As the tricuspid valve tube moves vertically using the holding member 32, the blocking member 60 formed at the tricuspid valve tube 30 can be moved. This configuration will be described in more detail referring to FIG. 4. Rubber materials, synthetic materials including soft plastic materials such as nylon that is biologically suitable, or metal materials such as a coil spring may be used for the tube. An exemplary embodiment that only the tricuspid valve tube is inserted into the sheath tube is shown in the drawings. However, in some cases, the coronary sinus tube may also be inserted into a separate sheath tube, and an exemplary embodiment that the coronary sinus tube and the tricuspid valve tube are simultaneously inserted into their respective sheath tubes is also available.

Figure 2:
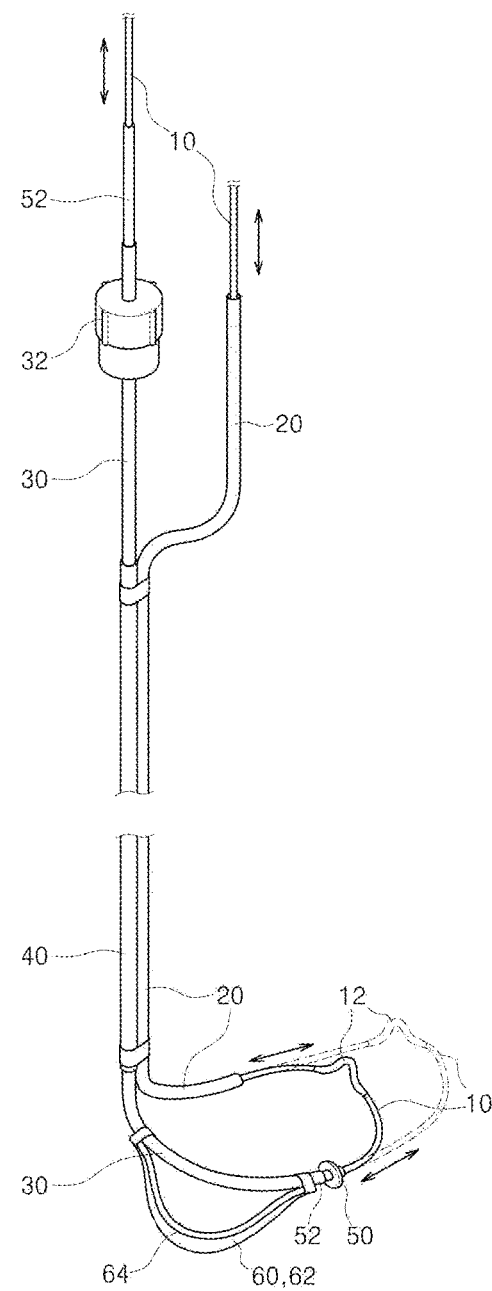
FIG. 2 is a view showing a method of varying a length of a cerclage wire in the device for transcatheter treatment for tricuspid regurgitation of FIG. 1.

FIG. 2 is a view showing a method of varying a length of a cerclage wire in the device for transcatheter treatment for tricuspid regurgitation of FIG. 1.

Referring to FIG. 2, the cerclage wire 10 is inserted into the coronary sinus tube 20 and the tricuspid valve tube 30, which are interconnected into one, like making one loop. If one side or both sides of the cerclage wire 10 are vertically moved at the upper side (that is, pulled or pushed), the loop formed by the cerclage wire 10 becomes larger or smaller, as shown in the drawings. According to this, proper tension can be maintained according to the size and the shape of a patient's heart, and the cerclage wire 10 may be squeezed so as to firmly hold a heart valve annulus. That is, the wire functions to squeeze a mitral annulus.

Figure 3:
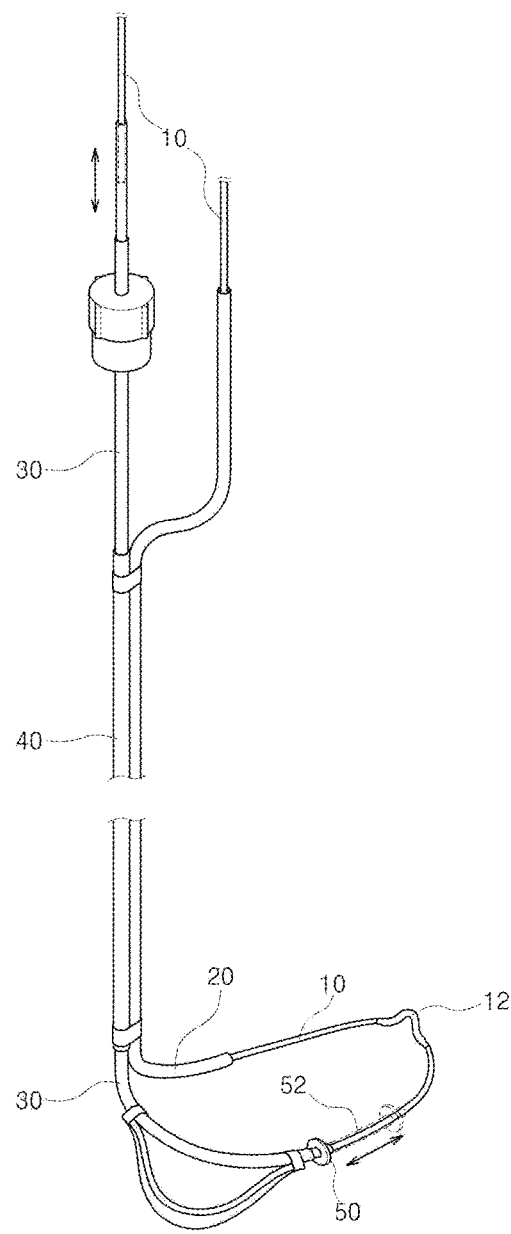
FIG. 3 is a view showing a method of moving a position of a stopper in the device for transcatheter treatment for tricuspid regurgitation of FIG. 1.

FIG. 3 is a view showing a method of moving a position of a stopper in the device for transcatheter treatment for tricuspid regurgitation of FIG. 1.

Referring to FIG. 3, the stopper 50 is fixed at the tube 52 for moving the stopper, which is structured to be inserted into the tricuspid valve tube 30. Here, if the tube 52 for moving the stopper is pushed or pulled at the upper part, the tube 52 for moving the stopper moves along the tricuspid valve tube 30, and the stopper 50 formed on the lower end of the tube 52 for moving stopper moves along the cerclage wire. Accordingly, a lower end of the tricuspid valve tube (a portion at which the tricuspid valve tube and the coronary sinus tube are separated from the stopper) forms a large or small curved line.

Movement of the stopper makes a portion of the tricuspid valve tube curved (in a reverse form), so as to be stably supported. As the stopper is located at a right ventricular outflow tract (RVOT) portion of the heart, the curved shape is held from the stopper to the portion at which the tricuspid valve tube and the coronary valve tube are separated, being kept slightly afloat. According to this, the tricuspid valve tube is floated over the tricuspid valve rather than to be in close contact with the periphery of the tricuspid valve, serving to prevent damage by the cerclage wire or the tricuspid valve tube to the tricuspid valve and functioning to less restrict movement of the valves and cusps. That is, movement of the stopper enables the stopper to stably support the tricuspid valve tube.

Figure 4:
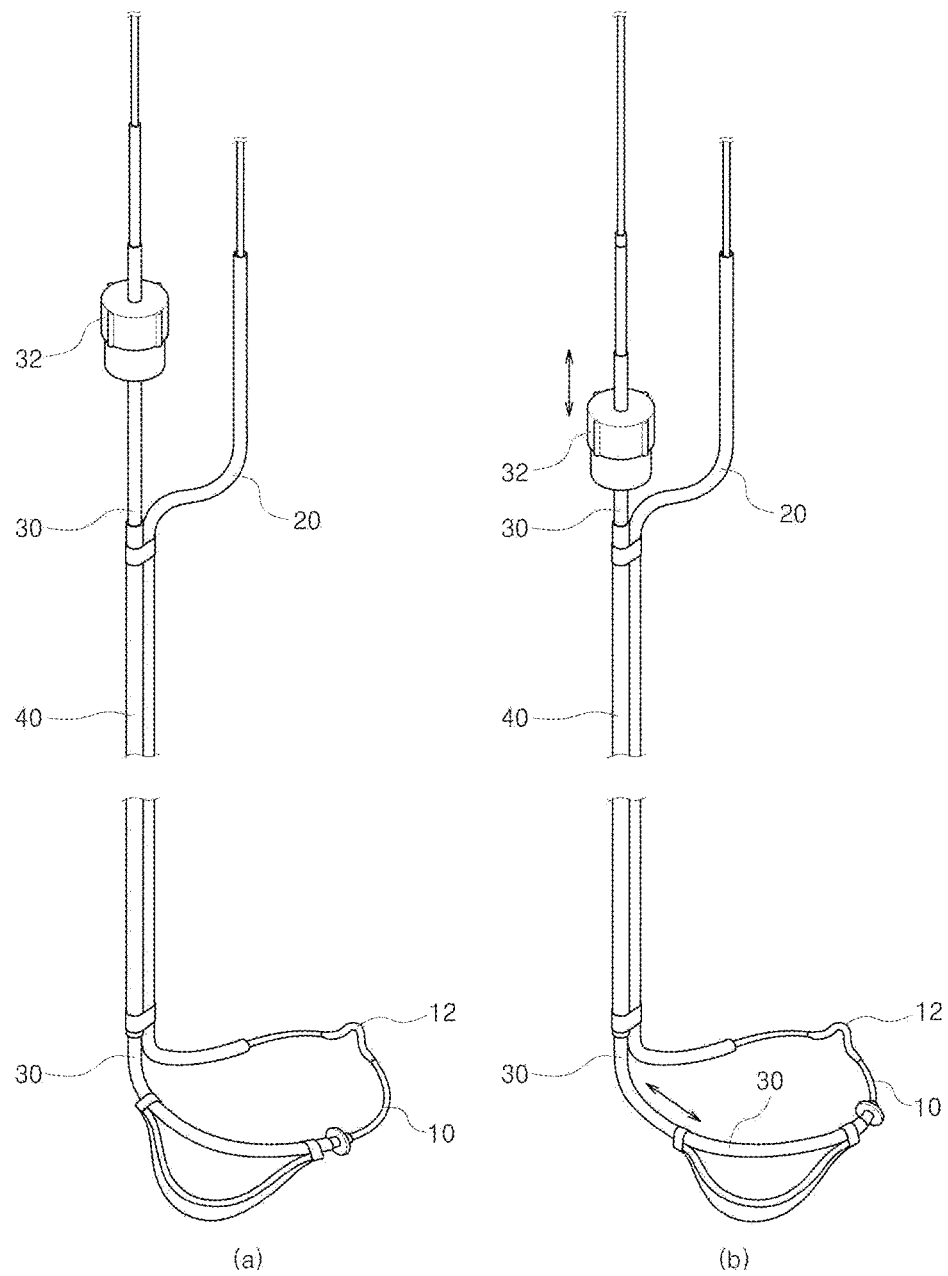
FIG. 4 is a view showing a method of varying the length of the tricuspid valve tube by means of a holding member in the device for transcatheter treatment for tricuspid regurgitation of FIG. 1, in which (a) shows the holding member before movement and (b) shows the holding member after movement.

FIG. 4 is a view showing a method of varying the length of the tricuspid valve tube by means of a holding member in the device for transcatheter treatment for tricuspid regurgitation of FIG. 1, in which (a) shows the holding member before movement and (b) shows the holding member after movement.

Referring to FIG. 4, the upper side of the tricuspid valve tube 30 is inserted into the sheath tube, and the sheath tube 40 and the coronary sinus tube 20 come into close contact with each other, allowing the coronary sinus tube 20 and the tricuspid valve tube 20 to be adjacent to each other within a predetermined region. A holding member 32 that can move the tricuspid valve tube 30 vertically along the sheath tube 40 is fixedly formed at the upper side of the tricuspid valve tube 30. According to vertical movement of the holding member 32, the tricuspid valve tube 30 moves vertically, enabling a position of the blocking member 50 formed in the tricuspid valve tube to be adjusted. Accordingly, the blocking member 60 can be adapted to the space (orifice) generated by incomplete closing of the tricuspid valve tube in the systole of the heart.

In other words, as the size and position of the blocking member which blocks the space (orifice) generated by incomplete closing of the tricuspid valve tube in the systole of the heart can vary, a doctor can proceed with treatment according to a size and a position of the space (orifice) caused by incomplete closing of the tricuspid valve which differs for each patient, through an angiography apparatus. Accordingly, probability of success in treatment can be drastically increased.

Figure 5:
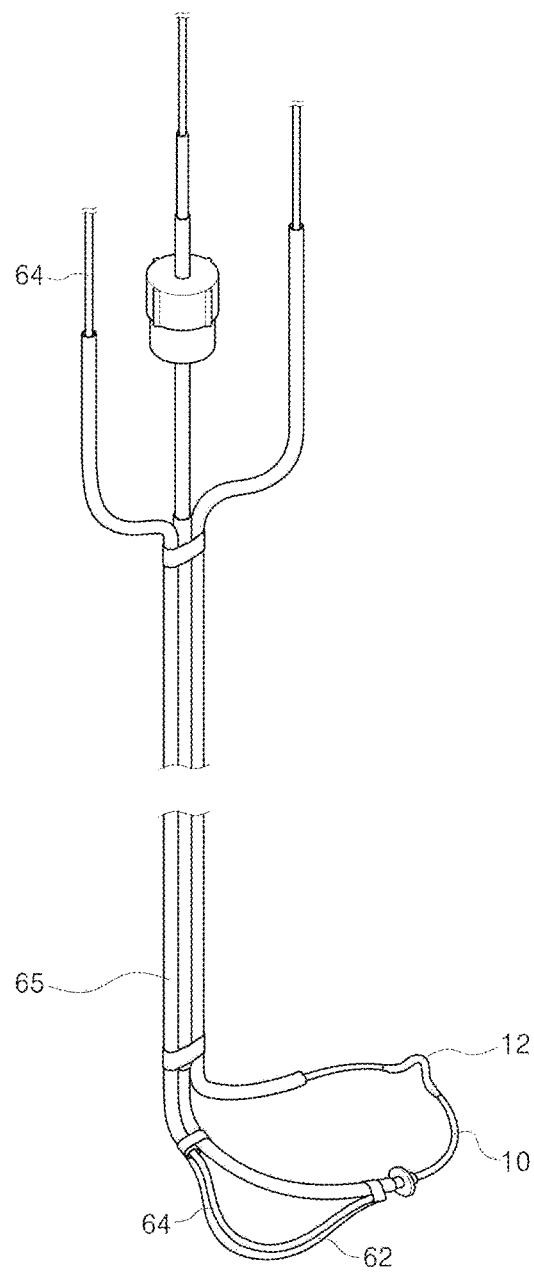
FIG. 5 is a perspective view of a device for transcatheter treatment for tricuspid regurgitation according to another exemplary embodiment of the present invention.
Figure 6:
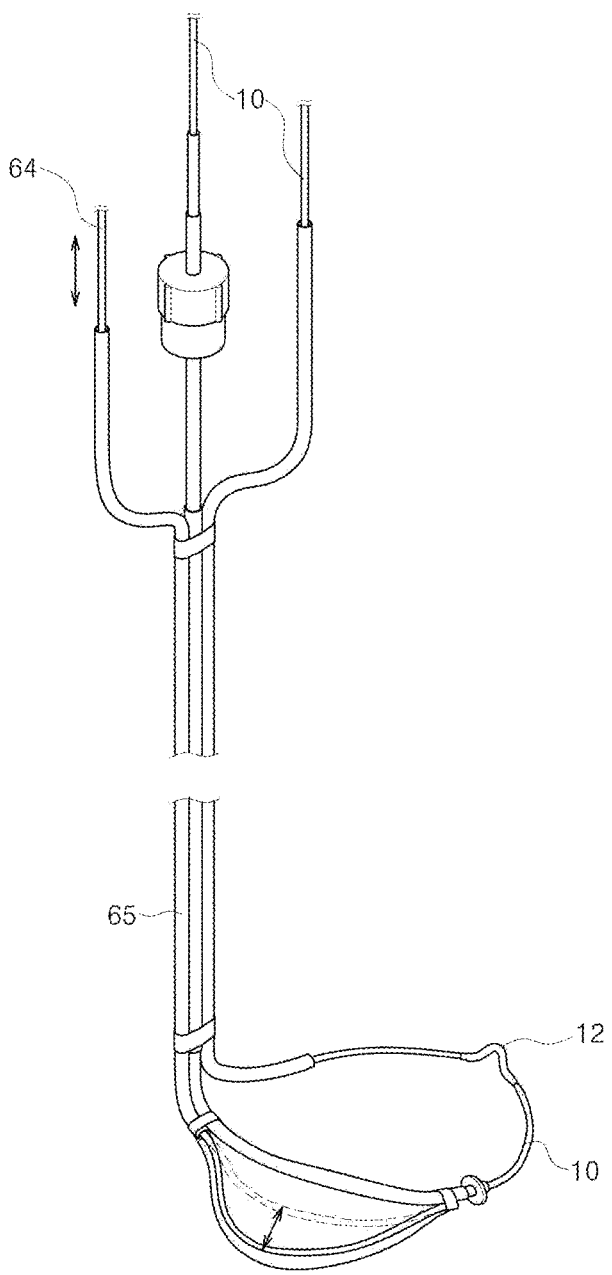
FIG. 6 is a view showing a support wire after a length thereof is changed in FIG. 5 (after the support wire is pulled up).

FIG. 5 is a perspective view of a device for transcatheter treatment for tricuspid regurgitation according to another exemplary embodiment of the present invention, and FIG. 6 is a view showing a support wire after a length thereof is changed in FIG. 5 (after the support wire is pulled up).

Referring to FIGS. 5 and 6, one side of the blocking membrane 62 is fixed at the tricuspid valve tube and supported by the support wire 64. The blocking membrane 62 is made of two or more layers, and the upper side of the support wire 64 is inserted into a tube 65 for support wire coupled to the tricuspid valve tube 30, and the lower side thereof is inserted movably between the blocking membranes. A lower end of the support wire 64 is fixed at a lower end of the tricuspid valve tube 30.

A space formed in the blocking membrane 62 by the support wire may be changed according to vertical movement of the support wire at an upper side. That is, according to the vertical movement of the support wire, the support wire at the lower part may be stretched or shortened, thereby causing the space made by the tricuspid valve tube and the support wire to be increased or decreased. According to this, the space created by the tricuspid valve tube and the support wire may be adjusted adaptively to the size of the space generated by incomplete closing of the tricuspid valve.

Naturally, a holding member as shown in the drawings may be formed at a tube for moving stopper, a support wire, and a cerclage wire, respectively, for vertical movement of the tube for moving stopper, movement of the support wire, and movement of the cerclage wire, although they are not shown in the drawings.

Figure 7:
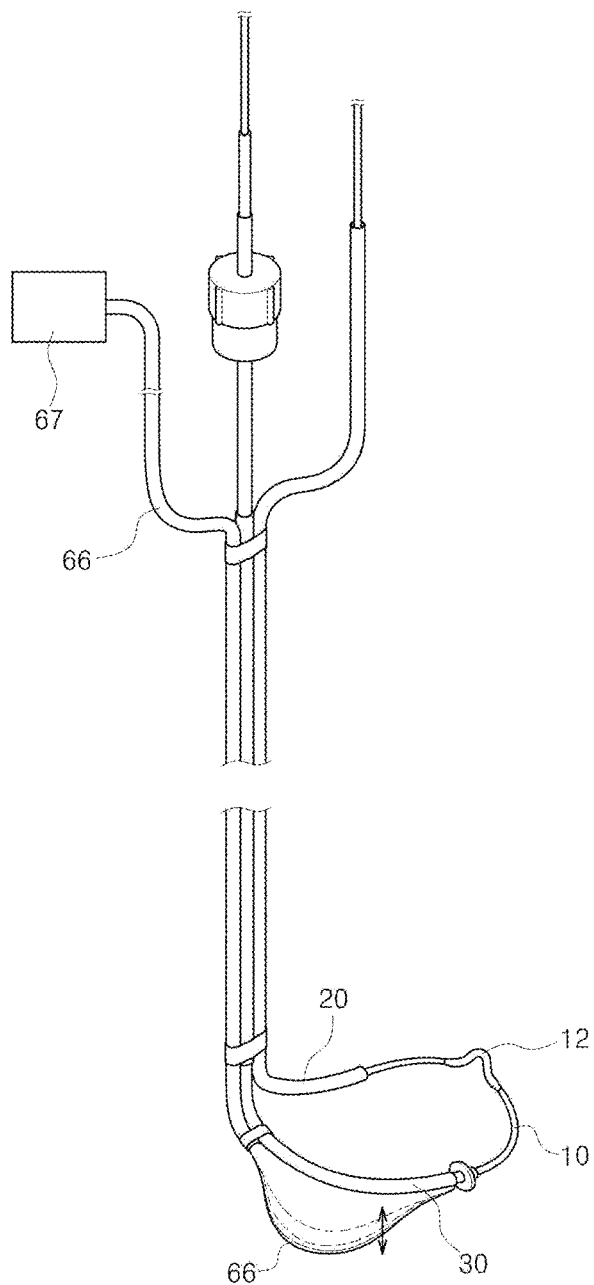
FIG. 7 is a perspective view of a device for transcatheter treatment for tricuspid regurgitation according to a still another exemplary embodiment of the present invention, to explain a method of installing a blocking balloon and changing a size of the blocking balloon.

FIG. 7 is a perspective view of the device for transcatheter treatment for tricuspid regurgitation according to a still another exemplary embodiment of the present invention, to explain a method of installing a blocking balloon 61 and changing a size of the blocking balloon 61.

Referring to FIG. 7, a blocking balloon 61 is fixed at the tricuspid valve tube 30, the blocking balloon 61 communicates with a tube 66 for balloon with maintaining airtightness therebetween, and the other end of the tube 67 for balloon is coupled to a balloon control hub 67. The balloon control hub 67 corresponds to a blower to supply air or oxygen. As the size of the blocking balloon 61 is changed depending upon the amount of air or oxygen supplied by the balloon control hub 67, the size of the blocking balloon can be adjusted adaptively to the size of the space generated by incomplete closing of the tricuspid valve tube in the systole of the heart.

Figure 8:
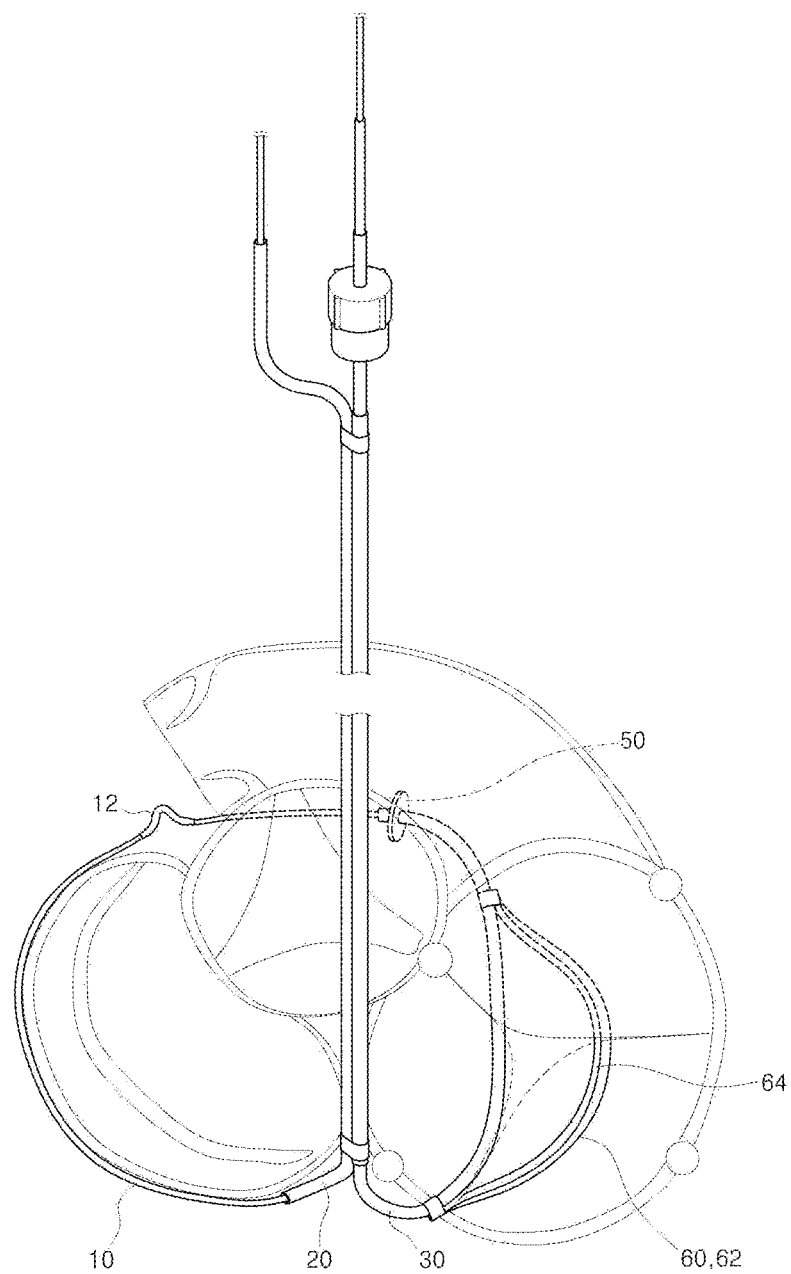
FIG. 8 is a view showing a shape of a device for transcatheter treatment for tricuspid regurgitation after performing treatment using the device for transcatheter treatment for tricuspid regurgitation according to the present invention is performed.
Figure 9:
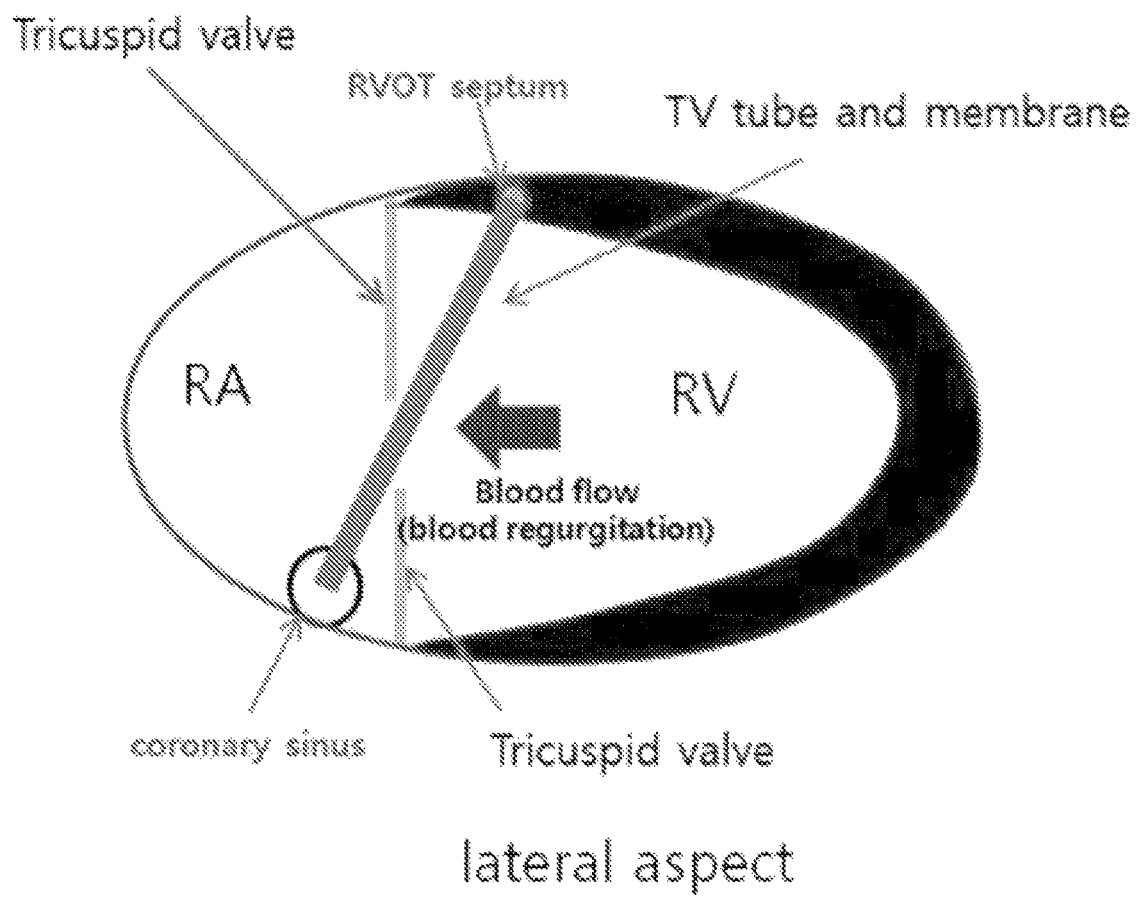
FIG. 9 is a view showing a principle of treating tricuspid regurgitation using a device for transcatheter treatment for tricuspid regurgitation according to the present invention.
Figure 10:
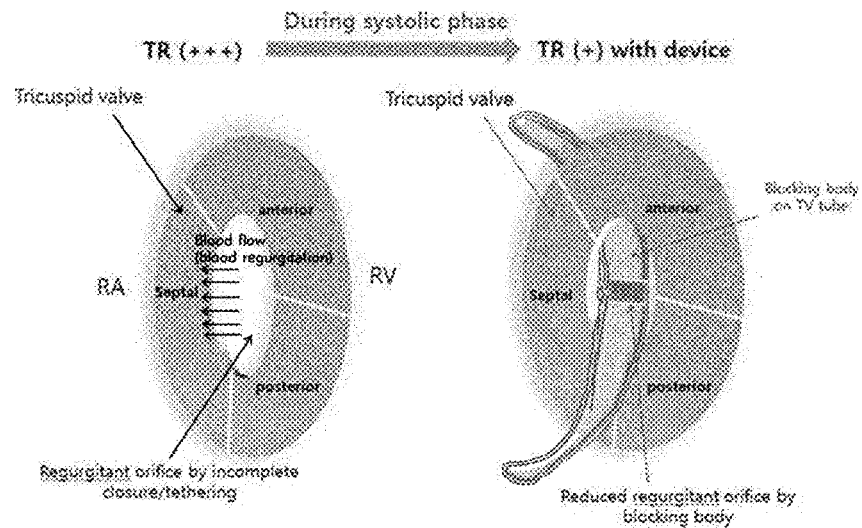
FIG. 10 is a view showing a device for transcatheter treatment for tricuspid regurgitation according to the present invention, blocking a space (orifice) in the tricuspid valve by passing in and out obliquely with the tricuspid valve.
Figure 11:
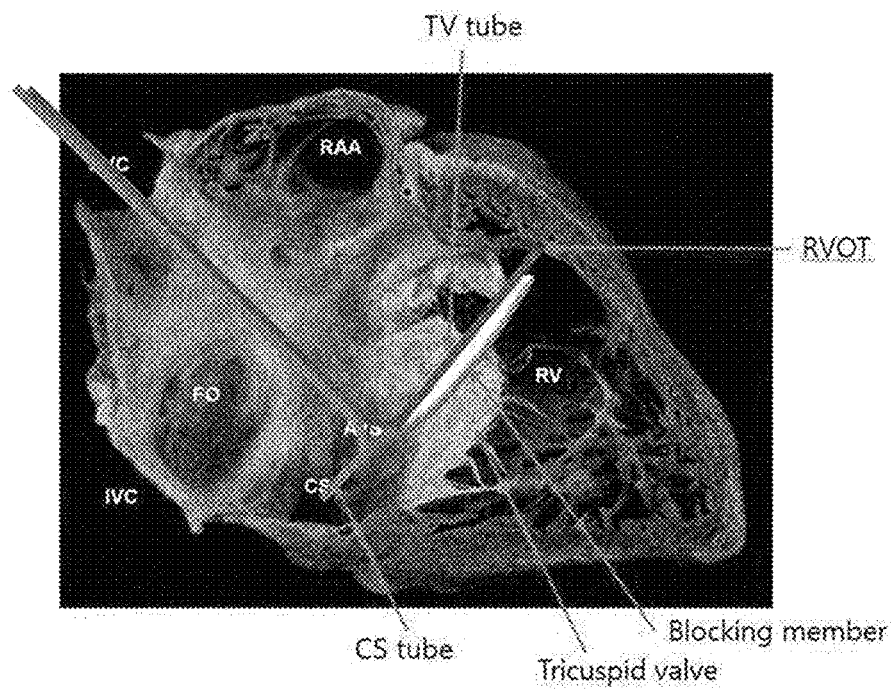
FIG. 11 is a view showing a position of a device for transcatheter treatment for tricuspid regurgitation in the heart.

FIG. 8 is a view showing a shape of a device for transcatheter treatment for tricuspid regurgitation after performing treatment using the device for transcatheter treatment for tricuspid regurgitation according to the present invention is performed, FIG. 9 is a view showing a principle of treating tricuspid regurgitation using a device for transcatheter treatment for tricuspid regurgitation according to the present invention, FIG. 10 is a view showing a device for transcatheter treatment for tricuspid regurgitation according to the present invention, blocking a space (orifice) in the tricuspid valve by passing in and out obliquely with the tricuspid valve, and FIG. 11 is a view showing a position of a device for transcatheter treatment for tricuspid regurgitation in the heart.

Referring to FIGS. 8 to 11, a condition that the blood flows backward from the right ventricle (RV) to the right atrium (RA) (that is, blood regurgitation) occurs in the tricuspid regurgitation patient because the tricuspid valve tube does not completely close, although the tricuspid valve must completely close in the systole of the heart. The device for transcatheter treatment for tricuspid regurgitation according to the present invention employs a principle of blocking a space generated by incomplete closing of the tricuspid valve with a blocking member thereof.

The tricuspid valve tube and the blocking membrane traverse (intersect, cross) the tricuspid valve in and out, to reach the coronary sinus (CS) and the RVOT septum. That is, the tricuspid valve tube and the blocking membrane are obliquely in parallel, traversing the tricuspid valve. Due to this structure, the blood of the right atrium (RA) is smoothly delivered to the right ventricle (RV) in the relaxation of the heart, and the blood of the right ventricle does not flow backward to the right atrium but flows to the pulmonary artery in the systole of the heart.

The device for transcatheter treatment for tricuspid regurgitation according to the present invention is fundamentally an improvement in a device for a mitral valve cerclage treatment, thus being able to accomplish treatment for tricuspid regurgitation together with treatment of the mitral valve regurgitation under a treatment procedure. That is, tricuspid regurgitation is mostly due to secondary or functional tricuspid regurgitation such as dysfunction of the left ventricle and dysfunction of the mitral valve, and the device for transcatheter treatment for tricuspid regurgitation according to the present invention results from modification in the device for a mitral valve cerclage treatment. Accordingly, the device for transcatheter treatment for tricuspid regurgitation according to the present invention can also be very effectively and efficiently used in tricuspid regurgitation treatment together with the mitral valve cerclage treatment.

Figure 12:
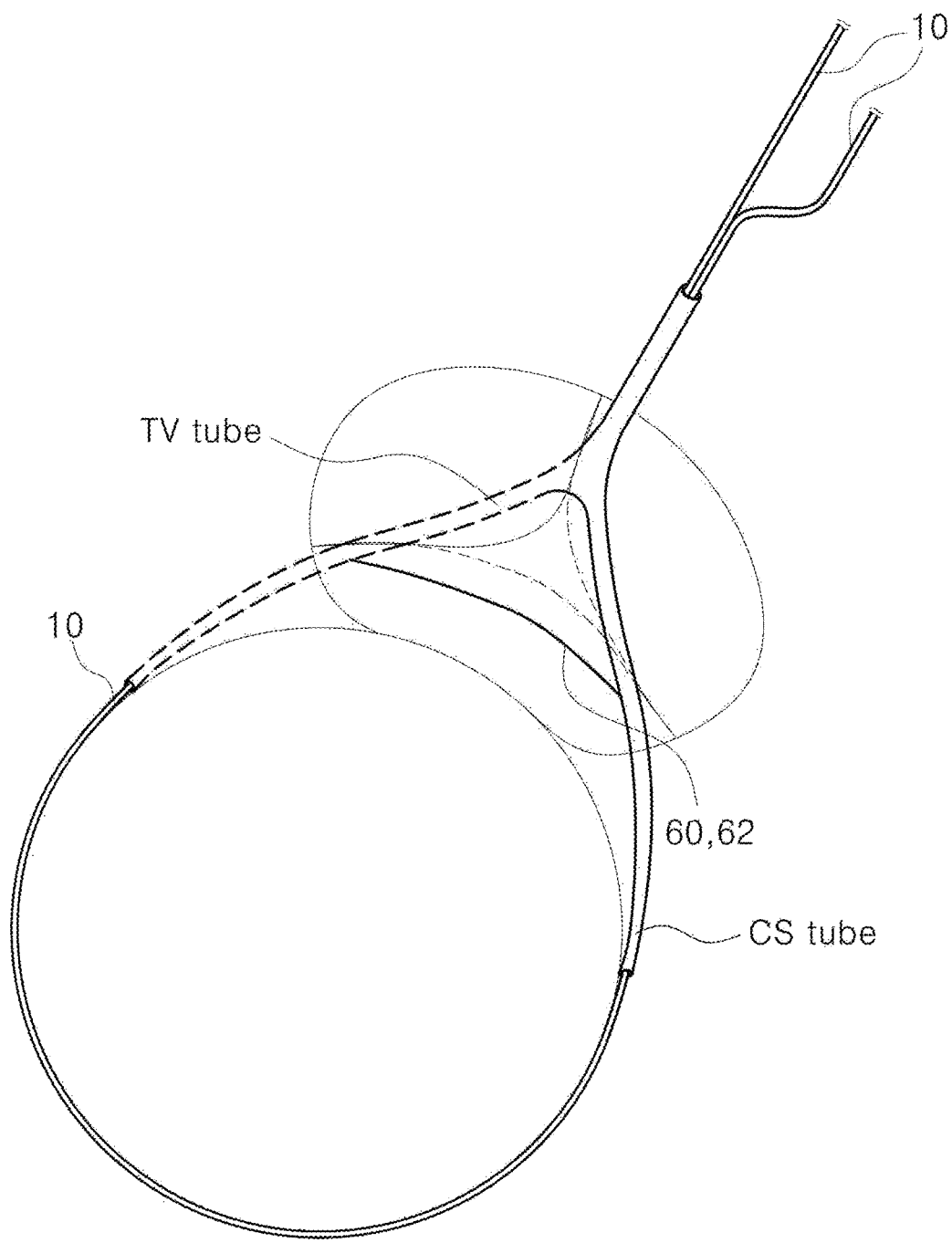
FIG. 12 is a view showing a shape of a device for transcatheter treatment for tricuspid regurgitation after performing treatment using the device transcatheter treatment for tricuspid regurgitation is performed according to a still another exemplary embodiment of the present invention.
Figure 13:
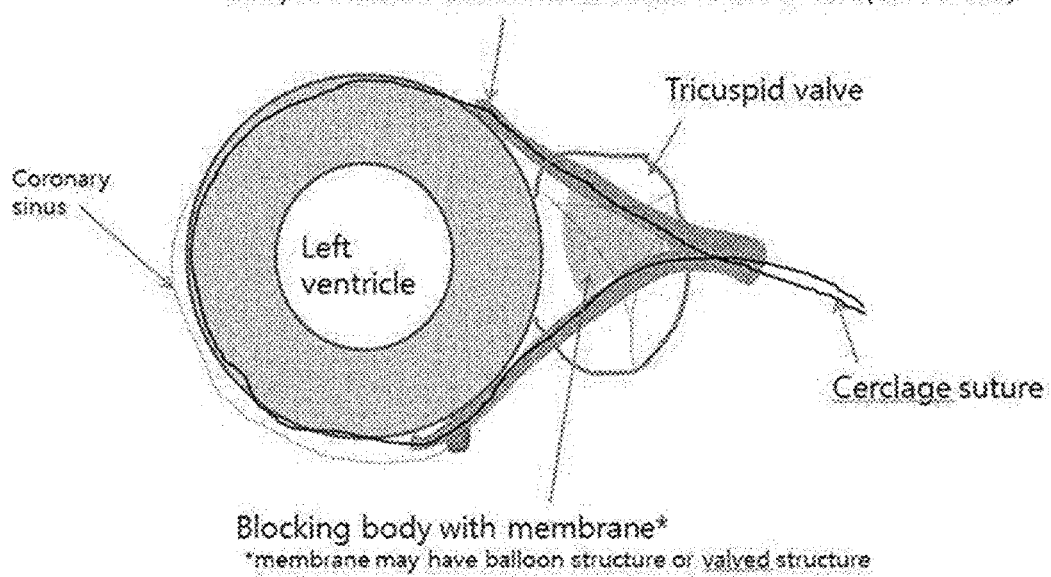
FIG. 13 is a view illustrating a treatment principle of a device for transcatheter treatment for tricuspid regurgitation shown in FIG. 12.

FIG. 12 is a view showing a shape of a device for transcatheter treatment for tricuspid regurgitation after performing treatment using a device for transcatheter treatment for tricuspid regurgitation according to a still another exemplary embodiment of the present invention, and FIG. 13 is a view illustrating a treatment principle of device for transcatheter treatment for tricuspid regurgitation shown in FIG. 12.

Referring to FIGS. 12 and 13, the coronary sinus tube and the tricuspid valve tube communicate with each other as a single tube within a predetermined length at the upper part, and they are separate from each other at the lower part. And, the blocking member for blocking the space generated by incomplete closing of the tricuspid valve is formed between the coronary sinus tube and the tricuspid valve tube. It is shown that the blocking member 60 takes a form of the blocking membrane 62, but it is possible that the blocking member 60 may also be applied to the blocking balloon.

Figure 14:
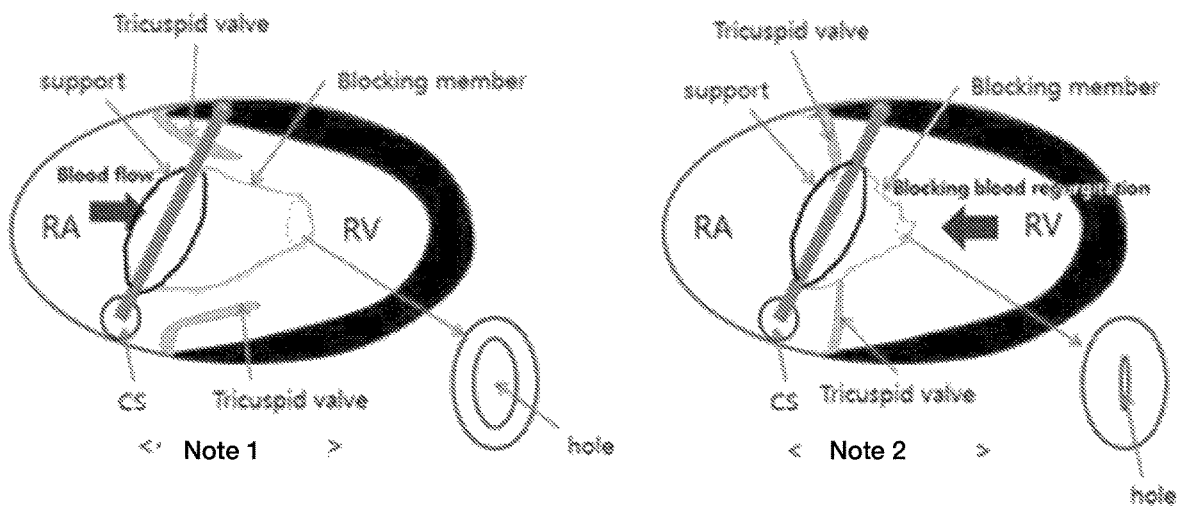
FIG. 14 is a view illustrating a treatment principle of tricuspid regurgitation using a device for transcatheter treatment for tricuspid regurgitation according to a yet still another exemplary embodiment of the present invention.

FIG. 14 is a view illustrating a treatment principle of tricuspid regurgitation using a device for transcatheter treatment for tricuspid regurgitation according to a yet still another exemplary embodiment of the present invention.

Referring to FIG. 14, the blocking member includes a support wire coupled to the tricuspid valve tube, and a blocking membrane coupled to the support wire. The support wire takes a form of a loop, and the blocking membrane is a membrane taking a form of funnel and having flexibility. The blocking membrane is located at the right ventricle, in the lower part of which a large orifice is formed by blood pressure in the relaxation of the heart, allowing the blood to flow smoothly. Conversely, the blocking member is contracted because of the blood pressure in the contraction of the heart due to a property of the membrane having flexibility, forming a small orifice at the lower part, thereby blocking blood regurgitation. Accordingly, the space generated by incomplete closing of the tricuspid valve can be efficiently blocked.

Although the present invention has been described with reference to exemplary embodiments shown in the drawings, it will be understood by those of ordinary skill in the art that the exemplary embodiments have been described for illustrative purposes, and various changes and modifications may be made without departing from the spirit and scope of the present invention as defined by the appended claims. Accordingly, it should be appreciated that the technical embodiments of the present invention described above are for illustrative purposes and they should not be construed in a limited manner.

The invention claimed is:

1. A transcatheter apparatus for treating a defective tricuspid valve comprising:
   a tricuspid valve (TV) catheter tube;
   an inner catheter tube inside the TV catheter tube and moveable back-and-forth within the TV catheter tube, wherein the inner catheter tube has a distal end;
   a cerclage wire inside the inner catheter tube;
   a blocking member on the TV catheter tube, wherein the blocking member is configured to block a space generated by incomplete closing of the tricuspid valve;
   a stopper at the distal end of the inner catheter tube, wherein the stopper moves back-and-forth by control of the inner catheter tube moving back-and-forth within the TV catheter tube.

2. The transcatheter apparatus of claim 1, wherein the blocking member has a curved shape.

3. The transcatheter apparatus of claim 1, wherein the blocking member comprises a flexible membrane.

4. The transcatheter apparatus of claim 3, further comprising a support tube and a support wire inside the support tube, wherein a shape of the blocking member is held by the support wire.

5. The transcatheter apparatus of claim 4, wherein the support wire is moveable back-and-forth within the support tube, and wherein a shape or size of the blocking member is changed by movement of the support wire.

6. The transcatheter apparatus of claim 1, wherein the blocking member is a balloon.

7. The transcatheter apparatus of claim 1, further comprising:
   a sheath tube through which the TV catheter tube travels;
   a holding member attached to the TV catheter tube;
   wherein the TV catheter tube moves back-and-forth relative to the sheath tube by control of the holding member.

8. The transcatheter apparatus of claim 1, further comprising a coronary sinus (CS) catheter tube through which the cerclage wire travels, wherein the blocking member is located between the CS catheter tube and the TV catheter tube.

9. The transcatheter apparatus of claim 8, wherein the TV catheter tube comprises a first lumen and the CS catheter tube comprises a second lumen, wherein the cerclage wire travels through the first lumen and the second lumen, and wherein the first lumen and second lumen are not in direct connection with each other.

10. The transcatheter apparatus of claim 1, further comprising:
    a sheath tube through which the TV catheter tube travels;
    a coronary sinus (CS) catheter tube through which the cerclage wire travels, wherein the blocking member is located between the CS catheter tube and the TV catheter tube.

11. The transcatheter apparatus of claim 10, wherein the sheath tube and the CS catheter tube are joined together in parallel arrangement at an intermediate portion of the CS catheter tube.

12. A method of treating a defective tricuspid valve in a patient's heart, comprising:
    having a transcatheter apparatus of claim 1;
    inserting the TV catheter tube into the patient's heart such that the blocking member traverses the tricuspid valve;
    adjusting the position of the stopper by moving the inner catheter tube within the TV catheter tube.

13. The method of claim 12, wherein the stopper is positioned to prevent an end of the TV catheter tube from piercing into an interventricular septum of the patient's heart.

14. The method of claim 13, wherein the blocking member is oriented obliquely with respect to the tricuspid valve.

15. The method of claim 13, wherein the transcatheter apparatus further comprises an arch member on the cerclage wire, and wherein the method further comprises positioning the arch member over a coronary artery of the heart.

16. The method of claim 13, further comprising forming a loop with the cerclage wire and changing a size of the loop by adjusting the cerclage wire.

17. The method of claim 12, wherein the transcatheter apparatus further comprises:
    a flexible membrane for the blocking member;
    a support tube and a support wire inside the support tube, wherein a shape of the blocking member is held by the support wire;
    wherein the method further comprises moving the support wire back-and-forth within the support tube to change a size or shape of the blocking member.

18. The method of claim 17, wherein the blocking member is oriented obliquely with respect to the tricuspid valve.

19. The method of claim 17, wherein the transcatheter apparatus further comprises an arch member on the cerclage wire, and wherein the method further comprises positioning the arch member over a coronary artery of the heart.

20. The method of claim 12, wherein the blocking member is oriented obliquely with respect to the tricuspid valve.

21. The method of claim 20, further comprising forming a loop with the cerclage wire and changing a size of the loop by adjusting the cerclage wire.

22. The method of claim 12, wherein the transcatheter apparatus further comprises:
    a sheath tube through which the TV catheter tube travels;
    a holding member attached to the TV catheter tube;
    wherein the method further comprises adjusting the position of the blocking member by moving the holding member.

23. The method of claim 12, wherein the transcatheter apparatus further comprises:
    a coronary sinus (CS) catheter tube through which the cerclage wire travels, wherein the blocking member is located between the CS catheter tube and the TV catheter tube;
    wherein the method further comprises inserting the CS catheter tube into a coronary sinus of the patient's heart.

24. The method of claim 23, wherein the transcatheter apparatus further comprises a sheath tube through which the TV catheter tube travels, wherein the sheath tube and the CS catheter tube are joined together in parallel arrangement at an intermediate portion of the CS catheter tube.

25. The method of claim 24, further comprising forming a loop with the cerclage wire and changing a size of the loop by adjusting the cerclage wire.

26. The method of claim 12, wherein the transcatheter apparatus further comprises an arch member on the cerclage wire, and wherein the method further comprises positioning the arch member over a coronary artery of the heart.

27. The method of claim 12, further comprising forming a loop with the cerclage wire and changing a size of the loop by adjusting the cerclage wire.

* * * * *